United States Patent
Rodriguez et al.

(10) Patent No.: US 9,678,060 B2
(45) Date of Patent: Jun. 13, 2017

(54) LUNASIN-INDUCED REGULATION OF DISEASE-RELATED GENE EXPRESSION

(75) Inventors: Raymond Rodriguez, Davis, CA (US); Alfredo F. Galvez, West Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1561 days.

(21) Appl. No.: 12/682,892

(22) PCT Filed: Oct. 10, 2008

(86) PCT No.: PCT/US2008/011650
§ 371 (c)(1),
(2), (4) Date: Aug. 2, 2010

(87) PCT Pub. No.: WO2009/051662
PCT Pub. Date: Apr. 23, 2009

(65) Prior Publication Data
US 2010/0291044 A1    Nov. 18, 2010

Related U.S. Application Data (60) Provisional application No. 60/999,053, filed on Oct. 14, 2007.

(51) Int. Cl.
*G01N 33/50* (2006.01)
*G01N 33/574* (2006.01)
*G01N 33/68* (2006.01)

(52) U.S. Cl.
CPC ....... *G01N 33/5011* (2013.01); *G01N 33/574* (2013.01); *G01N 33/6875* (2013.01)

(58) Field of Classification Search
None
See application file for complete search history.

(56) References Cited

U.S. PATENT DOCUMENTS

2005/0130170 A1   6/2005   Harvey

FOREIGN PATENT DOCUMENTS

WO    WO 2005-091823    10/2005
WO    WO 2005/091823  * 10/2006

OTHER PUBLICATIONS

Galvez et al. (Chemopreventive property of a soybean peptide (lunasin) that binds to deacetylated histones and inhibits acetylation, 2001, Cancer Research, vol. 61, pp. 7473-7478).*
Ren et al. (Peptide mapping of acetylated isoforms of histone H4 from mouse lymphosarcoma cells treated with histone deacetylase (HDACs) inhibitors, 2005, Journal of the American Society for Mass Spectrometry, vol. 16, pp. 1641-1653).*
Li et al. (Methylation and silencing of the Thrombospondin-1 promoter in human cancer, 1999, Oncogene, vol. 18, pp. 3284-3289).*
Desai et al. (UGT pharmacogenomics: implications for cancer risk and cancer therapeutics, 2003, Pharmacogenetics, vol. 13, pp. 517-523).*
Smith et al. (Mass spectrometric quantification of acetylation at specific lysines within the amino-terminal tail of histone H4, 2003, Analytical Biochemistry, vol. 316, pp. 23-33).*
Xudong Ma et al. "Epigenetics and Targeted Therapy in Acute Leukemia." Oncogene May 1999 vol. 18 (21) pp. 3284-3289.
Galvez AF, Chen N, Macasieb J, de Lumen BO. Chemopreventive property of a soybean peptide (lunasin) that binds to deacetylated histones and inhibits acetylation. Cancer Res. 2001;61:7473-7478.

* cited by examiner

*Primary Examiner* — Sean Aeder
(74) *Attorney, Agent, or Firm* — Adam Warwick Bell; Matthew Rupert Kaser (57) ABSTRACT

Methods are provided for screening a test compound for anti-neoplastic activity by providing a test compound to a cancer cell and measuring the acetylation of Lysine 16 of the N-terminal tail of histone H4. Methods are also provided for using a test compound for staging a cancer tissue and for measuring the degree of the test compound's anti-neoplastic activity upon a cancer tissue by providing a test compound to a cancer tissue sample and measuring the degree of methylation of nucleotides within the 5' region in the cancer tissue sample.

8 Claims, 7 Drawing Sheets

Figure 1. Effect of Lunasin on expression of UGT1A1 in HepG2 cells treated with Lunasin (asterisk activated; arrows upregulated)

Figure 2. Lunasin upregulates mRNA transcript levels of UGT1A1 and UGT1A3. RT-PCR of cDNA derived from Lunasin and non-Lunasin treated HepG2 liver cells using UGT1A1 and UGT1A3 primers. Actin RT-PCR products show equal levels of actin in cDNA Figure 3. Western blots of acid-extracted histones. Acid extracted histones isolated from HeLa cells were used in p300 histone acetylase reactions, immunoblotted and stained with antibodies to Ac-Lys5, Ac-Lys8, Ac-Lys12, and Ac-Lys16 (4 acetylation sites in histone H4 N-terminal tail). (-) is the histone template control, + NaB correspond to acid extracted histones from NaButyrate treated HeLa cells (posititve control), + Lun correspond to lunasin treated histone template and − Lun correspond to non-lunasin treated histone template used in p300 histone acetylase reaction. Boxed signals indicate increased acetylation by p300 acetylase enzyme.

Figure 4. Western blot of recombinant histone H4 stained with Ac-Lys 16. Recombinant H4 (rH4) was used as template in histone acetylase reactions using HAT enzymes, p300, hat1 and pCAF. Reaction products were immunoblotted and stained with Ac-Lys 16 antibody. Boxed signal indicates significant increase in acetylation from template control.

Figure 5. Western blot of THBS and PCR of ChIP DNA isolated with anti-Ac-H4 Lys16. THBS protein levels were determined in RWPE-1 and -2 cell lines treated with or without lunasin. PCR was conducted on ChIP DNA isolated with acetylated H4-Lys16 antibody, using primers derived from the promoter and exon 11 of the THBS gene.

Figure 8. Bar graph showing that Lunasin preferentially binds to deacetylated histone H4

Figure 9. Approximately 30% of genes upregulated by lunasin have transcription start sites within proximity to CpG islands in the human genome. The set of 121 genes upregulated by lunasin has significantly more CpG island in proximity to the transcription start site (0-2000 bp) compared to 7 randomly selected set of 121 genes (rnd1-7)) from the same microarray. Chi-square P value < 0.005.

Figure 10. PCR of bisulfite-treated RWPE-1 (R1) and RWPE-2 (R2) genomic DNA with unmethylated specific primers (6,7) and methylated specific primers (8,9) reveals CpG island methylation of the THBS1 promoter (*) in tumorigenic R2 cells but not in R1. PCR using methylated DNA control shows the 8,9 methylated primers recognizing methylated DNA at higher level than 6,7 primers that recognize unmethylated DNA.

RWPE-1 (SEQ ID No.1)

GTTTTTTGTTGGTGTGTGTTTATTGGTGGAGGAATTTTTAGGAATGTG
AGTGTTTTTTTAAAAGTGTGTGGTTTTTTTGTTTTGTTAGTTGTTGTG
TTTGAGTTGGTTTGTGAGTTTAGGGTTTTTGTTGTTTT
TTAGGAGTAA

RWPE-2 (SEQ ID No.2)

CGAGGGGTAGGTATTTTAACGAATGGTTTTTTGGTGTTTTTGCGTTTCGT
CGGTTTATTTTTTTTTTATAAAACGGGTTTAGTTTTTAGTATTTATTTTT
CGTTATTAATTAGGTATTTCGGGAGATTAGTTCGTTCGAAAGTTTTTGCG
TTATTTCGCGGGTTTTTTTAGGTGGTTTTTTTAGTTTCGTTTTCCTTCGGG
ATGTTTGTTGATTATTTCGAGTTCGCGTGGCGTAAGAGTACGAGCGTCGA
GTTCGTGCGCGTTAAGGTTGCGTGGGCGGGTATCGATTTTTTGAGAAGT
TTTAGTGTTTTAAGTTTCGATTTTCGTTTTTTTTATTTTTTAGTTGGAAA
GTTGCGCGTTAGGTAGCGGGGGGCGGAGAGAGGAGTTTAGATTGGTTTT
TATTTTTCGTTTTTTGTTCGGTCGTCGTTTATTGGTCGGAGGAATTTTTA
GGAATGCGAGCGTTTTTTTAAAAGCGCGCGGTTTTTTCGTTTTGTTAGT
CGTTGCGTTCGAGTTGGTTTGCGAGTTTAGGGTTTTTG
TCGTTTTTTAGGAGTAATTTTTATTTCGGACGTATAGG
TATTTTTCGCGTTTTTTTAGTTTTCGTCGTTTTCGTTA
TCGTTTTCGGTCGTCGCGTTTCGGTATATATAG GTAAGT
CGTTTTCGGCGGTCGTCGAGGATTAAAGTTGTTCGGGATATTTATTTGGA
GCGTTGAGGTTTAGTTTTTTTGGTGGA

Figure 11. DNA sequence of bisulfite treated genomic DNA corresponding to the CpG island found in the promoter and first exon of THBS-1 in RWPE-1 and RWPE-2 cells. Bold T's were unmethylated C's that were converted to T's by bisulfite treatment. Green highlighted T's in RWPE-1 correspond to CpGs that were not methylated and converted to Ts. Yellow highlighted C's within the CpG island of RWPE-2 were methylated and not converted to T's by bisulfite treatment. Underlined sequence correspond to the first exon and red highlight correspond to the transcription start site.

LUNASIN-INDUCED REGULATION OF DISEASE-RELATED GENE EXPRESSION

RELATIONSHIP TO OTHER APPLICATIONS

This application claims the benefit of U.S. Provisional application No. 60/999,053 filed 12 Oct. 2007 entitled "Lunasin-induced regulation of disease-related gene expression". This, and the following applications are hereby incorporated by reference for all purposes: 60/594,487 "Gene Expression Profiles In Normal And Tumorigenic Cells"; 60/261,217 "The Use of Lunasin Peptide as a Transcriptional Activator to Prevent Cancer and Related Methods for Treatment, Monitoring and Prognosis"; and PCT/US05/04868 "The Use of Lunasin Peptide as a Transcriptional Activator to Prevent Cancer and Related Methods for Treatment, Monitoring and Prognosis."

GOVERNMENT SUPPORT

This invention was made in part with government support under one or more grants from the UC Davis Center of Excellence for Nutritional Genomics and in part with government support under Grant No. P60MD00222 awarded by the National Institutes of Health (NIH). The government has certain rights in the invention."

FIELD OF THE INVENTION

The invention relates to disease-associated gene expression and to regulation of the expression of various genes by lunasin and related compounds.

BACKGROUND OF THE INVENTION

Lunasin is a 43 amino acid small subunit of a soybean 2S albumin. The polynucleotide encoding the lunasin peptide, and the peptide sequence of lunasin are known and disclosed in U.S. Pat. No. 6,544,956 (hereby incorporated by reference in its entirety) in which the lunasin peptide is encoded by bases 80-208 of SEQ ID NO:1, and the peptide is defined by residues 22-64 of SEQ ID NO:2. The carboxyl end of lunasin contains a chromatin-binding domain, a cell adhesion motif Arg-Gly-Asp (RGD) followed by eight Asp residues (Galvez and de Lumen, 1997; Galvez and de Lumen, 1999). The chromatin-binding domain consists of a 10-amino acid helical region homologous to a short conserved region found in other chromatin binding proteins (Aasland and Stewart, 1995). Mammalian studies provide evidence that lunasin may play a role in the cell cycle control (Galvez and de Lumen, 1999; Galvez et al., 2001; Jeong et al., 2002). For example, transfection of the lunasin gene into mammalian cells results in mitotic arrest and subsequent cell death (Galvez and de Lumen, 1999). In addition, exogenous addition of chemically synthesized lunasin to mammalian cells demonstrates that lunasin colocalizes with hypoacetylated chromatin; preferentially binds deacetylated histone H4 in vitro; and prevents histone H3 and H4 acetylation in vivo in the presence of a histone deacetylase inhibitor (Galvez et al., 2001). Acetylation and deacetylation of conserved histone N-terminal tails result in chromatin conformational changes that induce or suppress gene expression. It has been hypothesized that Lunasin modulates changes in chromatin organization by modifying histone tails, thereby, affecting gene expression that produces its anti-neoplastic properties. Recently, lunasin was isolated from barley and was reported to possess the same biological activity ascribed to chemically synthesized lunasin (Jeong et al., 2002).

Lunasin peptide has been shown to have anti-neoplastic properties (Galvez et al., 2001). Significant suppression of chemical carcinogen-induced, e.g. 7,12-dimethylbenz-[a]-anthracene (DMBA) and 3-methylcholanthrene (MCA), foci formation in C3H 10T1/2 mouse embryo fibroblast cells was observed when lunasin was added exogenously at nanomolar concentrations. In addition, topical application of lunasin inhibited skin tumorigenesis in female SENCAR mice. Lunasin peptide has also been shown to induce apoptosis in E1A-transfected C3H10T1/2 cells (Galvez et al., 2001) and suppress foci formation in E1A-transfected mouse fibroblast NIH 3T3 cells (Lam, et al., in press). E1A is a viral onco-protein that inactivates the Rb (retinoblastoma) tumor suppressor (Nevins, 1992). Furthermore, when C3H 10T1/2 and MCF-7 human breast cancer cells were treated with lunasin in the presence of the histone deacetylase inhibitor, sodium butyrate, a 10- to 95-fold reduction in acetylation of core histones H3 and H4 was observed (Galvez et al., 2001). The genome-wide reduction in core histone acetylation suggests an epigenetic mechanism of action for lunasin that can influence gene expression fundamental to carcinogenesis.

BRIEF DESCRIPTION OF THE INVENTION

Lunasin can act as an amplifier of gene expressions for genes activated by hormones, drugs, extracellular and other environmental stimuli. Amplification occurs by increasing chromatin accessibility in the promoter region of the gene by acetylation of lysine 16 at the amino-terminal ends of histone H4 of the nucleosome. Acetylation of H4Lysine 16 is important in making the promoter DNA accessible to transcriptional complexes.

The invention encompasses methods for upregulating the expression of one or more chemopreventative genes in a cell (or in a subject or tissue or cell culture) by specifically contacting lunasin (or a derivative or variant thereof) to the deacetylated Lysine 8 residue (Lys 8) of the N-terminal tail of histone H4, thereby allowing increased acetylation of Lysine 16 (Lys16), thereby upregulating gene expression of one or more chemopreventative or antineoplastic genes. Certain embodiments include demethylation of regions of the THBS gene, including the CpG island within the promoter region. In preferred embodiments the chemopreventative genes include one or more UGT1A gene(s) such as, for example, UGT1A1, UGT1A3, UGT1A6 and/or UGT1A10 and/or the thrombospondin gene (THBS). Methods used can be in vitro or in vivo and can be used to treat a whole organism or to treat tissues or cells.

Embodiments of the invention include a method for screening a test compound for anti-neoplastic activity, the method comprising (1) providing a test compound, providing a cell, measuring the acetylation of Lysine 16 of the N-terminal tail of histone H4, (2) exposing the cell to the test compound, and (3) re-measuring the acetylation of Lysine 16 of the N-terminal tail of histone H4 in the cell, wherein the degree of increase in acetylation of Lysine 16 of the N-terminal tail of histone H4 in the cell corresponds to the degree of anti-neoplastic activity of the test compound. Such a method may be used to screen any candidate antineoplastic compounds including but not limited to derivatives or variants of lunasin. Alternative methods for screening a test compound include measuring expression of various target genes such as UGT1A genes and/or the thrombospondin gene (THBS).

Certain embodiments of the invention include various therapeutic treatments, and in vivo and in vitro experimental procedures, that upregulate various chemopreventative genes as UGT1A genes and/or the thrombospondin gene (THBS) by the administration to a subject (or cell or cell culture) of a substance or substances that promotes demethylation of THBS and/or increased acetylation of the H4-Lys 16 in the promoter/CpG island of THBS.

Other embodiments of the invention include a method for upregulation of UGT1A1 enzyme, the method comprising administering to a cell an amount of lunasin or variant or functional equivalent thereof or administering a compound screened by the method above and identified by that method as having (putative) antineoplastic activity.

Various methods of the invention include demethylation of certain regions of the THBS gene, including the CpG island within its promoter (which is frequently found to be hypermethylated during cancer formation).

Other embodiments include methods which increase H4-Lys 16 acetylation in the promoter/CpG island of the THBS gene. This may be done following demethylation of the CpG island region of the THBS gene.

In the above methods demethylation of regions of THBS and increased acetylation of the H4-Lys 16 in the promoter/CpG island of THBS may be practiced in a therapy in concert by simultaneously or contemporaneously or sequentially administering to a subject a compound that induces THBS demethylation and a compound that increases acetylation of the H4-Lys 16. Such methods may include administration to a subject or a cell or cell culture a formulation containing lunasin or a derivative or variant thereof. In such methods lunasin or a related specie may be administered to a subject or animal or cell either together with or contemporaneously with a substance that promotes demethylation of THBS and increased acetylation of the H4-Lys 16 in the promoter/CpG island of THBS.

Other embodiments of the method include additionally quantifying the degree of methylation of THBS and/or acetylation of CPG island before and/or after administration of substances that promote demethylation and acetylation as described above.

Other embodiments include screening of putatively cancerous tissue (e.g., from a biopsy) and by comparing the expression profiles with those from tumorigenic and non-tumorigenic cells.

Other embodiments include a method for comparing the expression profiles of a first cell line and a second cell line treated with lunasin, the second cell line comprising tumorigenic clone of the first cell line, and wherein the first cell line is not tumorigenic.

Other aspects of the invention include the monitoring of the physiological state of a tissue or tumor by measuring either (i) the acetylation of Lysine 16 of the N-terminal tail of histone H4 in the cell, or (ii) the degree of methylation of THBS, or (iii) the degree of expression of chemopreventative genes such as, for example, UGT1A1, UGT1A3, UGT1A6, UGT1A10 and/or THBS.

The methods described herein may be practiced on a whole animal such as a mammal, a cell, a cell culture or a tissue or organ. In treatments that involve subjecting a cell to a combination of substances that affect gene expression, the substances may be administered to explanted cells from the subject ex vivo, and wherein the explanted cells are subsequently reimplanted into the subject.

In methods that comprise monitoring of acetylation, methylation or expression or genes or polynucleotide regions, such monitoring may take place before or after exposure to various substances, and in many cases such factors are measured both before and after exposure to determine the degree of anti-tumorigenic activity occurring in a sample. Such monitoring includes monitoring the degree of methylation of THBS and/or acetylation of the CPG island region of the thrombospondin gene before and after administration of substances that promote demethylation and acetylation as described above.

Other embodiments include a method for screening putatively cancerous biopsy tissue by measuring the degree of methylation of THBS and/or acetylation of the CPG island region of the thrombospondin gene.

DETAILED DESCRIPTION OF THE INVENTION

In the present disclosure the investigators determined that the lunasin peptide upregulates expression of chemopreventative genes by specifically binding to deacetylated Lysine 8 (Lys 8) of the N-terminal tail of histone H4, changing the structural conformation of the H4 tail to allow increased acetylation of Lysine 16 (Lys16) by histone acetylase enzymes. Acetylation of H4-Lys 16 is involved in creating the "open" conformation of chromatin required for upregulating gene expression. Immunostaining studies done on HepG2 liver cells using UGT1A1 primary antibody, show that the addition of 10 μM of lunasin to the growth media can upregulate expression levels of UGT1A1 and its isoforms. RT-PCR using primers specific to the 9 expressed UGT1A family of genes revealed the significant upregulation of UGT1A1, UGT1A3 UGT1A6 and UGT1A10. the investigators hypothesize that the upregulation of UGT1A genes by lunasin leads to the significant reduction of PhIP-induced prostate cancer formation in rats.

Lunasin exposure effects gene expression. The gene expression profiles resulting from lunasin exposure correlate with anti-neoplastic activity at a cellular level and can be used in methods for screening potential anti-neoplastic agents. Additionally, these gene expression profiles can be used in methods for treatment (both prophylactic and active) and in monitoring of disease states or risk factors of individuals. The gene expression profiles can be monitored by the use of microarrays used to measure the expression of particular sets of genes.

In the present disclosure the investigators analyzed changes in gene expression profiles of normal (RWPE-1) and malignant (RWPE-2) prostate epithelial cell lines after 24 hour exposure to synthetic lunasin. Results disclosed herein support the anti-neoplastic property of lunasin and help elucidate its molecular mechanism. Various genes found by this study to be up-regulated by lunasin are known to play a role in cell growth, differentiation and tumor suppression and other important physiological activity directly or indirectly related to neoplastic transformation. It is therefore reasoned that lunasin suppresses neoplastic transformation by up-regulating various genes.

Epigenetic Phenomena and Multistage Carcinogenesis

A number of studies have shown that tumor development may be accompanied by a number of phenomena. These phenomena may be assessed using multivariate analysis to determine the progression or remission of a tumor in vivo. Such phenomena include clinical stage as determined by pathology of biopsy sample, serum levels of tumor marker(s), other markers such as, but not limited to, chromosome deletion, chromosome gain, cell surface markers, oncogene activity, biopsy Gleason score, degree of aneuploidy, and the like. (See, for example Feneley and Partin (2001) *Urol. Clin. North Am.*, 28 (3): 443-458; Frankfurt et al. (1985) Cancer Res., 45 (3): 1418-1423; Araujo et al. (2007) Dis. Colon Rectum., 50 (11): 1800-1810; Vasudevan et al. (2005) World J. Surg., 29 (3): 317-324, incorporated herein by reference in their entirety.)

Many other studies have implicated degree of cytosine methylation (5-methylcytosine) as a prognosticator of tumor development. For example, Holliday and Jeggo (1985) reported that there was considerable evidence that genes can be activated by loss of methylation or inactivated by de novo methylation. Hypomethylation, that is, a reduction in 5-methylcytosine versus cytosine ratio present in a gene, was frequently observed in tumor cells. They speculated that the extent of karyotypic instability and hypomethylation showed some correlation with the stage of tumor progression. Del Senno et al. (1989) demonstrated that overall c-myc proto-oncogene methylation levels were significantly reduced in carcinomas. Furthermore, they reported a significant correlation between disease invasiveness (such as, for example, grade and/or stage) and methylation level was found. (Holliday and Jeggo (1985) Cancer Surv., 4 (3): 557-581 and Del Senno et al. (1989) J. Urol., 142 (1): 146-149, incorporated herein by reference in their entirety.)

Separately, Ohtani-Fujita et al. (1993) found that two transcription factors important for the promoter activity of the retinoblastoma gene, an activating transcription factor (ATF)-like factor and the retinoblastoma binding factor 1, did not bind when their recognition sequences on the promoter were CpG methylated in vitro. Counts and Goodman (1995) found correlations between extent of methylation of two candidate oncogenes, Ha-ras and raf, with mouse liver tumorgenesis. Bennett et al. (2008) reported methylation of candidate tumor suppressor genes (SLC5A8, IRX1, and EBF3) in head and neck squamous cell carcinoma. (See Ohtani-Fujita et al. (1993) Oncogene, 8 (4): 1063-1067; Counts and Goodman (1995) Prog. Clin. Biol. Res., 391: 81-101; Bennett et al. (2008) Cancer Res. 68 (12): 4494-4499; incorporated herein by reference in their entirety. See also Rice et al. (1998) Oncogene., 17 (14): 1807-1812 (BRCA1); Goodman and Counts (1993) Environ. Health Perspect., 101 Suppl. 5: 169-172 (Ha-ras); and Hogg et al. (2002) Eur. J. Cancer, 38 (12): 1585-1592 (RASSF1A); all of which are herein incorporated by reference in their entirety.) Such analytical methods may be used to monitor progression of a tumor, remission of a tumor, or both, used in combination with the instant invention as disclosed herein.

Monitoring the expression of lunasin-upregulated genes can be employed in a number of methods useful in therapy, in drug screening and in research into anti-neoplastic compounds. Since many of these genes are tumor suppressors, are involved in apoptosis or have other anti-neoplastic functions, it can be reasoned that an increase in the expression of such genes indicates an increase in anti-neoplastic activity. If this increase in expression occurs in response to the administration of a drug (such as lunasin) then the increase in expression can reasonably be used as a quantitative marker that correlates with the degree of anti-neoplastic effectiveness of the drug treatment. Thus methods involving measurement of gene expression can be used to monitor efficacy of treatment, and to predict likely clinical outcomes. In drug screening, an animal or cell culture is exposed to a compound, and the expression of one or a plurality of genes is monitored to screen putative drug candidates. The greater the average increase in gene expression of the genes in a particular panel (e.g., a panel of genes listed in Table 1 or Table 2), the higher the score of the drug candidate. Such prioritization is routinely used by drug discovery companies. Gene expression profiles may be produced using arrays (microarrays) and quantitatively scored by measuring the average increase in gene expression for a panel of genes in response to exposure to a set quantity of a compound for a set time. The score may be weighted by ascribing greater weight to specific genes. For example, a panel of genes may be selected to include the 121 genes were up-regulated in RPWE-1 in this study. Particular weight may be given to the genes that are known tumor-suppressors (e.g., PRKAR1A, PKA, TOB1, ERBB2IP, and ERBIN). Algorithms for scoring and weighting expression array results are well known in the art and one of skill could readily create or adapt an algorithm for use with the present methods.

The invention encompasses a method for treatment and monitoring of a subject having a neoplastic disease. The method comprises administering lunasin (or related or derived compounds) to the subject, and monitoring the change in expression levels of at least one gene selected from a set of genes known to be up-regulated by lunasin. Clinical symptoms may simultaneously be monitored to measure disease progression and/or the efficacy of treatment before, during and after the administration of lunasin.

Additionally, the invention also provides a method for using a test compound for staging a cancer tissue, the method comprising: providing a test compound, providing a cancer tissue sample, measuring the degree of methylation of nucleotides within the 5' region of a gene in the cancer tissue sample, comparing the degree of methylation of the gene with that from the gene of a non-cancer tissue sample, wherein a relative difference in degree of methylation correlates with the stage of the cancer tissue.

The invention further provides a method for using a test compound for measuring the degree of the test compound's anti-neoplastic activity upon a cancer tissue, the method resulting in a decrease in metastatic potential of the cancer tissue, the method comprising: providing a test compound, providing a cancer tissue sample, measuring the degree of methylation of nucleotides within the 5' region of a gene in the cancer tissue sample, exposing the cancer tissue to the test compound, measuring the degree of methylation of nucleotides within the 5' region of a gene in the exposed cancer tissue sample, comparing the degree of methylation of the gene with that from the gene of the non-exposed cancer tissue sample, wherein a second relative difference in degree of methylation corresponds to the degree of anti-neoplastic activity of the test compound upon the cancer tissue, the method resulting in a decrease in metastatic potential of the cancer tissue.

In one embodiment of any of the methods disclosed herein the 5' region of a gene comprises a CpG island in the promoter region of the gene. In a preferred embodiment the 5' region of the gene from the cancer tissue is hypomethylated compared to that of the 5' region of the gene from the non-cancer tissue. In a more preferred embodiment the gene is an oncogene. In an alternative preferred embodiment the gene is a cell surface marker. Such markers are frequently associated with increased metastatic potential. Exemplary cell surface markers include, but are not limited to CD133 (Prominin-1), chemokine CXCL13, sialidase, CD163, MUC1 mucin, RACK1, matrix metalloproteinases (MMP)-7, MMP-13, and the like.

In an alternative preferred embodiment the 5' region of the gene from the cancer tissue is hypermethylated compared to that of the 5' region of the gene from the non-cancer tissue. In more preferred embodiment the gene is selected from the group consisting of tumor suppressor genes and chemopreventative genes. In a most preferred embodiment the gene is the thrombospondin gene. In a most preferred embodiment the test compound is a variant or derivative of lunasin. In a more preferred embodiment of the method, a two-fold increase in methylation of the 5' region of the gene from the exposed cancer tissue compared with the methylation of the 5' region of the gene from the non-exposed cancer tissue corresponds to a decrease in the metastatic potential of the cancer tissue. In an alternative more preferred embodiment of the method, a two-fold decrease in methylation of the 5' region of the gene from the exposed cancer tissue compared with the methylation of the 5' region of the gene from the non-exposed cancer tissue corresponds to a decrease in the metastatic potential of the cancer tissue. In a preferred embodiment the method further comprises measuring the acetylation of Lysine 16 of the N-terminal tail of histone H4, wherein the degree of increase in acetylation of Lysine 16 of the N-terminal tail of histone H4 in the cancer tissue corresponds to the degree of anti-neoplastic activity of the test compound, the method resulting in a decrease in metastatic potential of the cancer tissue. In a more preferred embodiment of the method disclosed herein a two-fold increase in acetylation of Lysine 16 of the N-terminal tail of histone H4 corresponds to the classification of the test compound as having anti-neoplastic activity, the method resulting in a decrease in metastatic potential of the cancer tissue By monitoring one or a plurality of the up-regulated genes disclosed in this study before, during and after the administration of lunasin, efficacy of treatment may be monitored, and clinical outcomes can be better predicted. Such monitoring may be used to determine appropriate treatment and drug dosages.

The invention further encompasses a method for prophylactically treating and monitoring a subject having one of more cancer risk factors. The method comprises administering lunasin (or related or derived compounds) and monitoring expression levels of at least one gene selected from a set of genes known to be up-regulated by lunasin.

The invention further encompasses a method for monitoring anti-neoplastic activity in cell culture or in a subject during treatment. The method comprises taking a baseline reading of gene expression for at least one gene selected from a set of genes known to be up-regulated by lunasin; administering lunasin (or a derived or related compound, or providing some other treatment to the subject or cell culture); and then re-measuring the expression of at least one of the genes being monitored. Such a method may be useful for research to determine the efficacy of various drugs, combinations of drugs and formulations to treat or prevent neoplasia. Such drugs may include lunasin, optionally in combination with other neoplastic compounds and adjuvants.

The invention also includes microarrays comprising a at least one or a plurality of genes known to be up-regulated by lunasin by at least two-fold (the term "plurality" is means two or more). In certain embodiments, the microarray may include some or all of the genes up-regulated in RPWE-1 normal cells. Such a microarray may be employed in the above methods for monitoring the gene expression profile of a subject (or cell culture) treated lunasin (or a derived or related compound). By looking at changes in the gene expression profile, a qualitative and/or quantitative assessment can be deduced as to the degree to which genes are up-regulated in response to a treatment, and therefore the effectiveness of a treatment may be determined.

The invention further includes methods for screening compounds for anti-neoplastic activity using the arrays described herein. Such methods involve exposure of cultured cells, tissues, organs or whole animals to a test compound, and the measurement of expression of a plurality of genes before and after exposure to the test compound. The microarray used may include any desired number of genes up-regulated in the presence of lunasin.

Microarrays are well known in the art and consist of a plurality of polynucleotides arranged regularly on a substrate such as paper, nylon or other type of membrane, filter, gel, polymer, chip, glass slide, or any other suitable support. The polynucleotides on the substrate bind complementary polynucleotides in a sample, thereby forming a hybridization complex and allowing sensitive and accurate detection. The polynucleotides may be cDNAs of gene open reading frames (or parts of genes) that bind specifically to complimentary to mRNAs. Often the polynucleotides are short oligonucleotides of between about 6 and 25 bases in length. In some instances, the mRNAs of the sample may be used to create an amplified cDNA library (using PCR) and this library may then be screened using an array. In the present case, a microarray may include one or more polynucleotides or oligonucleotides derived from of the 123 genes shown in this disclosure to be up-regulated by lunasin by at least two-fold.

In the present disclosure, the term "polynucleotide" refers to an oligonucleotide, nucleotide, or polynucleotide, and fragments thereof, and to DNA or RNA of genomic or synthetic origin which may be single- or double-stranded, and represent the sense or antisense strand.

The above methods may include exposure of a subject or cell culture, or ex-vivo or in vitro tissue or organ to lunasin or related or derived compounds. In the present disclosure "related or derived compounds" include variations of lunasin such as a lunasin peptide sequence altered by addition, deletion or substitution of one or more amino acid. Guidance in determining which amino acid residues may be substituted, inserted, or deleted without abolishing biological or immunological activity may be found using computer programs well known in the art, for example, LASERGENE software (DNASTAR Inc., Madison Wis.). Variant peptides of lunasin may have at least 97% amino acid sequence identity over 43 amino acids with the lunasin peptide. In other embodiments, the variant peptide may have different degrees of identity such as at least 95%, 90%, 85%, 80%, 75%, 70%, or 60% or less identity with lunasin. Variants can be made using any of a variety of methods well known in the art. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. The changes can be made at any site in the lunasin sequence. Mutants may be screened for the optimal anti-neoplastic activity, revealed for example, by the microarray screening assay disclosed herein. Thus, a suitable variant is one which would activate at least particular genes of interest, such as PKA, TOB1, ERBIN, NIP3, TSP1, BUB1B, TTK, PSMC6, USP1 and the like, in normal cells, or would activate a minimum number of genes or markers, such as at least 25 genes or markers, at least 50 genes or markers, at least 75 genes or markers and so on, in a non-malignant cell.

The invention also includes methods for preventing neoplastic growth in an organism, a cell, cell culture, tissue of organ comprising administering an agent, wherein the agent up-regulates the activity or expression of at least one, two, three, four, five, six or more genes selected from those shown to be up-regulated by lunasin by at least two-fold. The agent is generally lunasin or a related or derived compound.

The effects and applications of lunasin-induced gene expression are disclosed in the following experimental examples.

Example 1

Lunasin Upregulation of UGT1A1 and its Effect on PhIP-Induced Carcinogenesis.

Prostate cancer is the most common malignancy and leading cause of cancer death among men that disproportionately affect African Americans relative to other ethnic/racial groups. The development of chemoprevention strategies that includes introducing complementary and alternative medicine (CAM) practices such as diet and nutritional supplementation to high-risk populations should help limit incidence of the disease and minimize health disparities. The Uridine diphosphate Glycosyl Transferases 1 (UGT1) family of genes are the enzymes involved in glucuronidation and elimination of many lipophilic xenobiotics and endobiotics, including bilirubin and the chemical carcinogen 2-amino-1-methyl-6-phenylimidazo[4,5-b]pyridine (PhIP), to more water-soluble compounds. PhIP is a heterocyclic amine formed in meats cooked at high temperature that causes prostate cancer in rats. There is growing evidence that the presence of UGT1A1 promoter polymorphisms among African-American populations with lower glucuronidation rates and expression levels of UGT1A1 may lead to higher incidence of prostate cancer. It should be noted that the allele frequencies that reduce UGT1A1 expression is high in African-American, rare in Caucasians and not detected in Asians. The primary role of UGT1A1 enzyme is to reduce bilirubin levels in neonatal infants and since bilirubin levels in Africans are significantly lower than Caucasians and Asians (because of more efficient photo-oxidation of bilirubin), it is possible that the Africans have higher frequencies of polymorphism that lower expression of UGT1A1 because of lesser need for the enzyme at birth. Since there is a need for this enzyme later in life to detoxify PhIP, the lower expression levels of UGT1A1 enzyme make the African-Americans more likely susceptible to the prostate cancer-inducing effects of PhIP.

Results/Hypothesis: The lunasin peptide has been shown to upregulate expression of chemopreventative genes, by specifically binding to deacetylated Lysine 8 (Lys 8) of the N-terminal tail of histone H4, changing the structural conformation of the H4 tail to allow increased acetylation of Lysine 16 (Lys16) by histone acetylase enzymes. Acetylation of H4-Lys 16 is involved in creating the "open" conformation of chromatin required for upregulating gene expression. Immunostaining studies done on HepG2 liver cells using UGT1A1 primary antibody, show that the addition of 10 uM of lunasin to the growth media can upregulate expression levels of UGT1A1 and its isoforms. RT-PCR using primers specific to the 9 expressed UGT1A family of genes revealed the significant upregulation of UGT1A1, UGT1A3 UGT1A6 and UGT1A10. We hypothesize that the upregulation of UGT1A genes by lunasin leads to the significant reduction of PhIP-induced prostate cancer formation in rats.

Experimental Design: Cell culture experiments are conducted to validate preliminary immunostaining results, followed by RT-PCR using primers specific to the 9 members of the UGT1A family of proteins to identify upregulated and activated gene products as modulated by lunasin treatment. Real-time quantitative RT-PCR is conducted to measure differences in transcription levels. Chromatin H4-Lysine 16 acetylation of lunasin upregulated and trans-activated genes is determined by using chromatin immunoprecipitation (ChIP) and hybridizing ChIP-fractionated genomic DNA to a custom-made tiled genome microarray (Ilumina platform) that span the 200 kb region of Chromosome 2 containing the UGT1A family of genes. The experiments suggest that Lunasin-enriched soy protein extracts can act as a chemo-preventative agent an humans and may be tested in a dietary intervention study using the PhiP-induced rat prostate cancer model.

The proposed research lays the scientific foundation for the use of lunasin-enriched soy protein extract as a chemo-preventative supplement against prostate cancer. Since we are testing its chemopreventative effect against the carcino-gen responsible for the increased prostate cancer risk associated with cooked meat consumption, the development of a comprehensive CAM strategy that includes lunasin supplementation and increased soy consumption is anticipated to help in reducing prostate cancer incidence among African-American men, the most at risk minority population due in part because of their genetic predisposition to low UGT1A1 expression, and a traditional diet low in soy consumption but rich in cooked and grilled meat.

Figure 1:
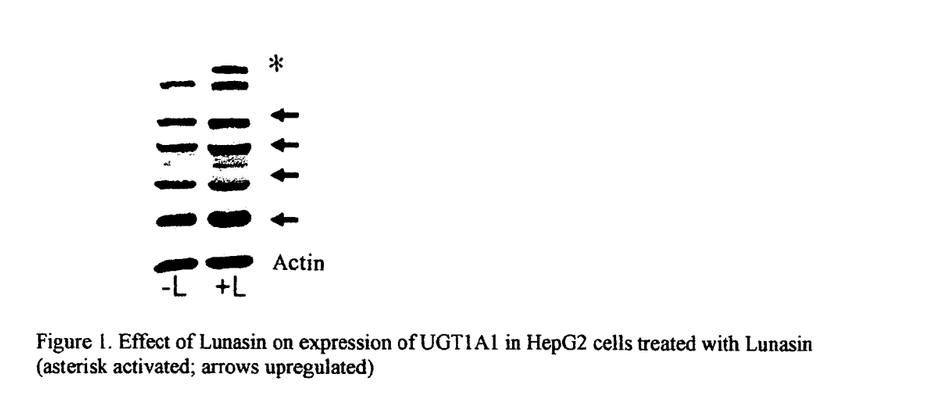
FIG. 1. An electrophoresis gel showing Lunasin-induced expression of UGT1A1 in HepG2 cells.
Figure 2:
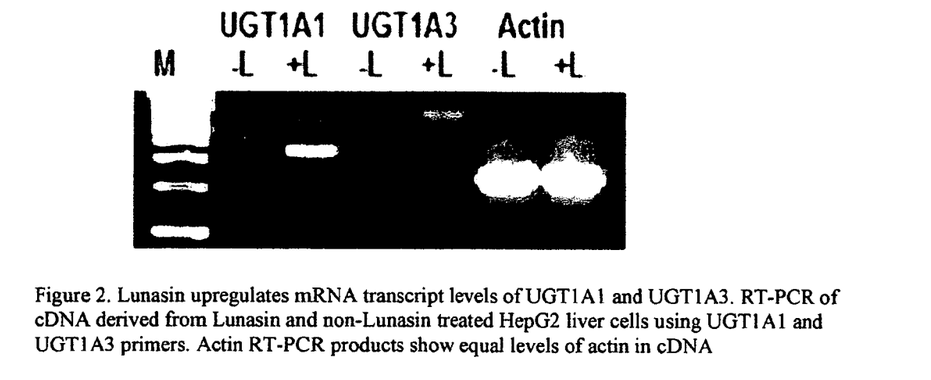
FIG. 2. An electrophoresis gel showing Lunasin-induced mRNA transcript levels of UGT1A1 and UGT1A3.

See FIG. 1 that shows results of experiments showing the effect of lunasin on expression of UGT1A1 isomers in HepG2 cells treated with or without lunasin (asterisk, indicate activated UGT1A isomer: arrows, upregulated UGT1A isomers). Actin control show equal loading of protein samples. These results show that (1) that Lunasin upregulates UGT1A1 protein levels; (2) Lunasin upregulates UGT1A1 mRNA levels See FIG. 2 that shows results of experiments showing the effect of lunasin on mRNA transcript levels of UGT1A1 and UGT1A3 in HepG2 cells. These results show that Lunasin upregulates UGT1A1 mRNA levels Example 2

Lunasin Upregulates Chemopreventative Genes by Increasing H4-Lys 16 Acetylation
A. Micorarray Experiments.

To determine the genetic changes associated with lunasin treatment, the gene expression profiles of non-tumorigenic (RWPE-1) (SEQ ID No.2) and tumorigenic (RWPE-2) (SEQ ID No.2) prostate cells treated with synthetic lunasin were assessed using microarray analysis. Results show that of the 14500 genes interrogated, 123 genes had a greater than twofold change in expression in the cells exposed to 2 µM lunasin for 24 hours (40). Of these genes, 121 genes were up-regulated in RWPE-1 cells and only two genes were up-regulated in RWPE-2 cells. No genes were down-regulated in either non-tumorigenic or tumorigenic epithelial cells treated with 2 µM lunasin. Genes that were up-regulated in RWPE-1 cells include genes that are involved in preventing cancer formation such as tumor suppression, pro-apoptosis, mitotic checkpoints and the control of cell division.

The microarray results suggest that lunasin can act as a transcriptional activator of genes that protect normal cells from transformation. These findings are in contrast to the previous mechanistic models suggesting that lunasin prevents normal cell transformation into tumors by inhibiting the acetylation of hypoacetylated histones H3 and H4 (11). It is believed that blocking the acetylation of these histones results in chromatin condensation and transcriptional silencing of oncogenes even in the absence or inactivation of tumor suppressors such as Rb (retinoblastoma protein). In a recent study, however, lunasin-treated NIH 3T3 cells (pre-treated for 24 h) transfected with the E1A oncogene showed a five-fold increase in p21/WAF1/Cip1 protein levels, eight days after E1A transfection. The protein p21/WAF1/Cip1 is a potent and universal inhibitor of cyclin-dependent kinases, which are major control points of cell cycle progression. The microarray results did not show upregulation of p21/WAF1/Cip1 within 24 hours, however, the gene SP3, a transcriptional activator of p21/WAF1/Cip, was upregulated by lunasin at 24 hours, which can explain the later increase in expression of p21/WAF1/Cip1 in the NIH 3T3 cells.

In addition, the microarray results help explain the 70% reduction of foci formation observed when C3H/T101/2 cells pre-treated with lunasin are exposed to the chemical carcinogens, DMBA) and MCA. A single 24 hour exposure of these cells to as little as 125 nM lunasin was sufficient to suppress foci formation in chemical carcinogenesis assays that lasted for six weeks. We speculate that the 24 hour pre-treatment of C3H/T101/2 cells with lunasin upregulates expression of chemopreventative genes that protect the cells from transformation induced by DMBA and MCA.

B. Histone Acetylation Experiments

Inhibition of histone acetylation and hypoacetylated histones are by nature correlated with transcriptional silencing and downregulation of genes. How then can lunasin, which inhibits H3 and H4 N-terminal tail acetylation, act as a transcriptional activator? To answer this question, the inventors determined the effect of lunasin on the acetylation of specific lysine residues on the H4 N-terminal tail (Lys −5, −8, 12 and 16) using the PCAF, Hat1 and p300 histone acetylase enzymes and acid-extracted core histones as substrate.

Results show that lunasin significantly inhibits H4-Lys 8 acetylation in PCAF (33% inhibition), Hat1 (30%) and p300 (23.5%) treated basal core histones, indicating that lunasin is binding specifically to H4-Lys 8, preventing its acetylation by PCAF, Hat1 and p300. PCAF did not acetylate H4-Lys 12 and H4-Lys 16 and partially aceylated H4-Lys 5 (7%). Hat1 was able to acetylate H4-Lys 5, 8 and 12 but not Lys 16. Lunasin treatment did not reduce H4-Lys12 acetylation by p300 and Hat1 and H4-Lys 5 by pCAF and Hat1 indicating that Lunasin does not bind to H4-Lys12 and H4-Lys 5. However, there was a significant increase in H4-Lys16 acetylation (22%) by p300 and (30%) by Hat1 in lunasin-treated core histones which suggests that lunasin by virtue of its binding to deacetylated H4-Lys 8, may have changed the conformation of the H4-tail, allowing p300 and Hat1 to acetylate H4-Lys 16.

Figure 3:
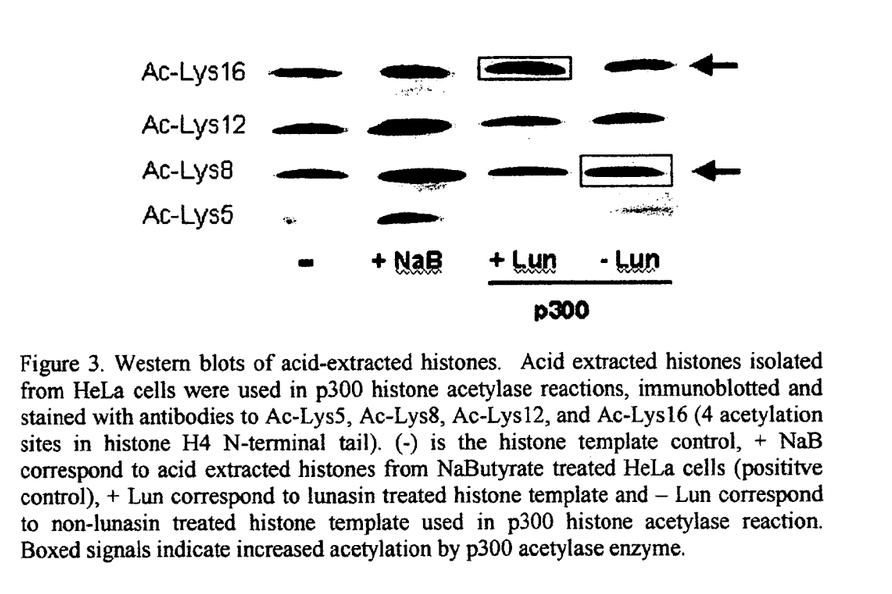
FIG. 3. Western blots of acid-extracted histones. Acid extracted histones isolated from HeLa cells were used in p300 histone acetylase reactions, immunoblotted and stained with antibodies to Ac-Lys5, Ac-Lys8, Ac-Lys12, and Ac-Lys16 (4 acetylation sites in histone H4 N-terminal tail). (−) is the histone template control, +NaB correspond to acid extracted histones from NaButyrate treated HeLa cells (positive control), +Lun correspond to lunasin treated histone template and −Lun correspond to non-lunasin treated histone template used in p300 histone acetylase reaction. Boxed signals indicate increased acetylation by p300 acetylase enzyme.

See FIG. 3 that shows Immunostaining of p300 (HAT) reaction products using acid-extracted histones. These results indicate that (1) Reduced Ac-Lys8 by Lunasin suggests histone binding/masking; (2) Increased Ac-Lys16 by Lunasin suggests H4 tail conformational changes to allow p300 access to Lys16. This experiment also shows that Lunasin upregulates gene expression only in normal prostate cells; that Lunasin has binding affinity to deacetylated Lys8 in histone H4; that Lunasin increases Lys16 acetylation; and that Lys16 acetylation disrupts chromatin condensation by destabilizing internucleosomal binding.

Crystal structure of core histones has revealed internucleosomal secondary structures as a result of the binding of the highly basic H4 amino acids 16-24 to a region of extreme acidity on the exposed face of the H2A-H2B histone dimer in an adjacent nucleosome. The acetylation of H4-Lys 16 help destabilize the nucleosome higher order structure, leading to the release of internucleosome connection, exposure of TATA box to TBP binding (or other transcriptional activators) and gene expression. Lunasin can upregulate expression of chemopreventative genes by virtue of its ability to increase H4-Lys 16 acetylation.

Histone acetylation experiments using recombinant H4 as substrate has confirmed lunasin binding to H4-Lys 8 but there was a loss of Lys16 acetylation using p300 and Hat1 in both lunasin-treated and non-treated recombinant H4. However the secondary co-activator pCAF which minimally acetylates H4-Lys16 when acid extracted histone is used as template, showed that it can significantly increase H4-Lys16 acetylation, when using recombinant H4 as template. Recombinant histone H4 which is unmodified (without any histone marks like acetylation) simulates a hypoacetylated histone H4 template. The loss of H4-Lys16 acetylation in the hypoacetylated H4 template can explain the inability of lunasin to upregulate chemopreventative genes in tumor cells.

Figure 4:
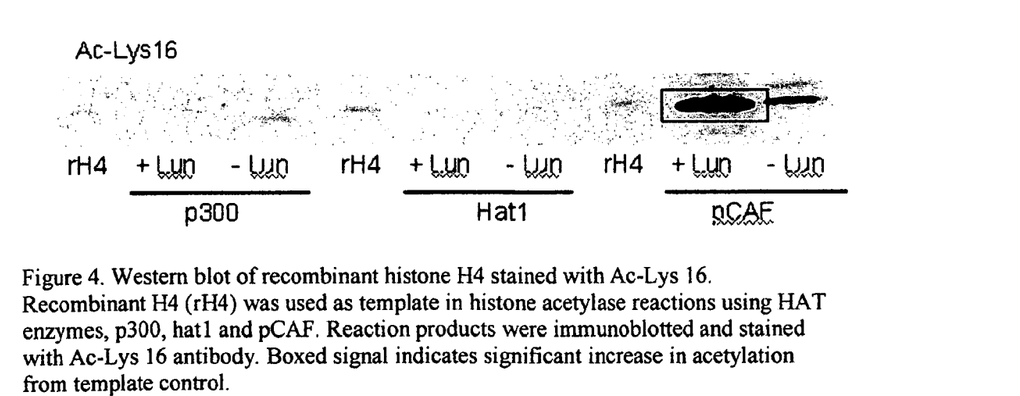
FIG. 4. Western blot of recombinant histone H4 stained with Ac-Lys 16. Recombinant H4 (rH4) was used as template in histone acetylase reactions using HAT enzymes, p300, hat1 and pCAF. Reaction products were immunoblotted and stained with Ac-Lys 16 antibody. Boxed signal indicates significant increase in acetylation from template control.

See FIG. 4 that shows a Western blot of recombinant histone H4 stained with Ac-Lys 16. Recombinant H4 (rH4) was used as template in histone acetylase reactions using HAT enzymes, p300, hat1 and pCAF. Reaction products were immunoblotted and stained with Ac-Lys 16 antibody. Boxed signal indicates significant increase in acetylation from template control. The results show that (1) HAT enzymes (p300 and Hat1) can not acetylate Lys16 using hypoacetylated recombinant H4 as a template; (2) Histone hypoacetylation is associated with DNA (CpG islands) hypermethylation during cancer formation; and (3) H4 hypoacetylation leads to loss of Lys16 acetylation and effect of lunasin on upregulation of chemopreventive genes in tumor cells.

Figure 9:
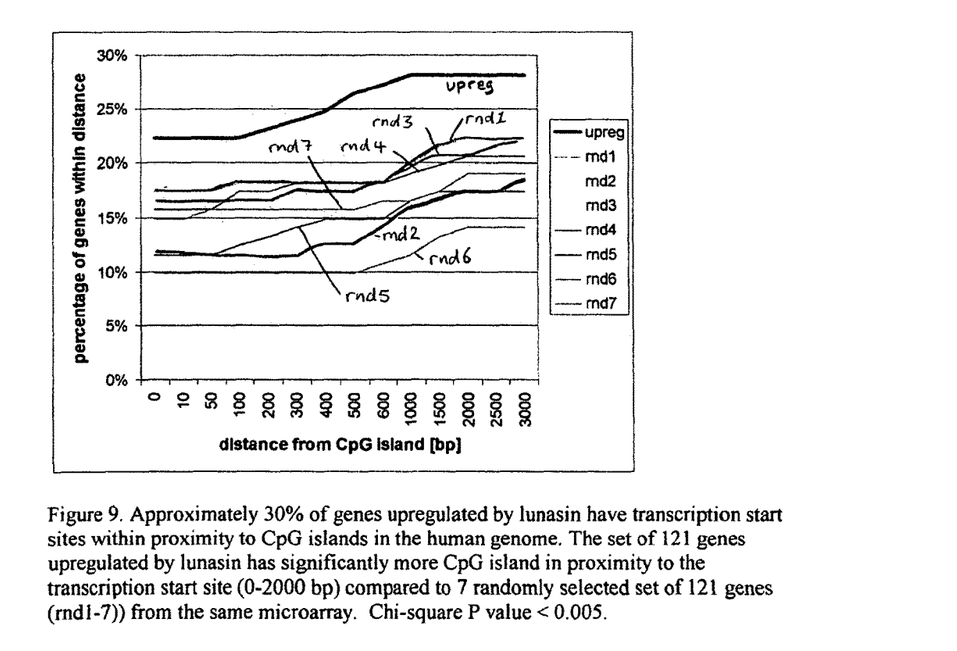
FIG. 9. Approximately 30% of genes upregulated by lunasin have transcription start sites within proximity to CpG islands in the human genome. The set of 121 genes upregulated by lunasin has significantly more CpG island in proximity to the transcription start site (0-2000 bp) compared to 7 randomly selected set of 121 genes (rnd1-7) from the same microarray. Chi-square P value <0.005.

One of the lunasin-upregulated genes identified from the microarray experiment is the thrombospondin gene (THBS). Western blot analysis shows that THBS is upregulated only in the non-tumorigenic (RWPE-1) cell line and is silenced in the tumorigenic RWPE-2 prostate cells, validating the microarray results (FIG. 9). THBS contains a CpG island within its promoter which together with other chemopreventative genes and tumor suppressors are frequently found to be hypermethylated during cancer formation. Since DNA hypermethylation of CpG islands is associated with histone hypoacetylation, we wanted to determine if there is a loss of H4-Lys16 acetylation within this region of the gene by conducting PCR on chromatin immunoprecipitated (ChIP) DNA using acetylated H4-Lys16 antibody and primers derived from the promoter/CpG island and exon 11 of the thrombospondin gene. Results from PCR of ChIP DNA shows that there is indeed loss of H4-Lys 16 acetylation in the tumorigenic cell line but only in the promoter/CpG island. Also, there is a significant increase in H4-Lys16 acetylation in the lunasin-treated RWPE-1 (non-tumorigenic) which mirrors the increase of THBS protein levels on the Western blot. The loss of H4-Lys16 acetylation on CpG island of the THBS promoter in tumor prostate cells leads to the silencing of the THBS gene and the inability of lunasin to increase H4-Lys16 acetylation and upregulate expression in tumorigenic cell lines.

Figure 5:
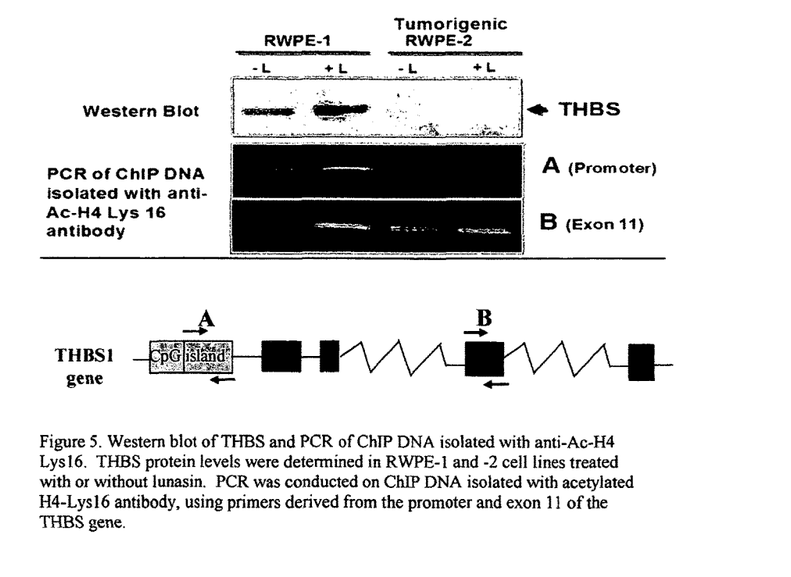
FIG. 5. Western blot of THBS and PCR of ChIP DNA isolated with anti-Ac-H4 Lys16. THBS protein levels were determined in RWPE-1 (SEQ ID No.1) and RWPE-2 (SEQ ID No.2) cell lines treated with or without lunasin. PCR was conducted on ChIP DNA isolated with acetylated H4-Lys16 antibody, using primers derived from the promoter and exon 11 of the THBS gene.
Figure 6:
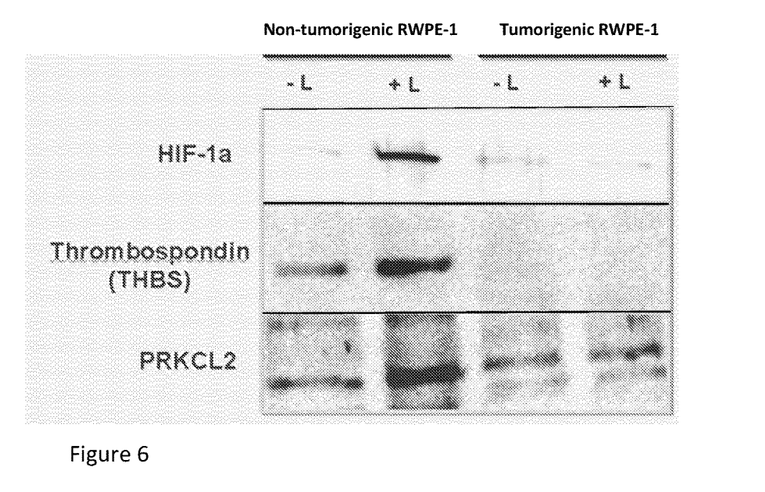
FIG. 6. Western blot showing upregulation of chemopreventative genes by lunasin in normal, but not tumorigenic prostate cells.
Figure 7:
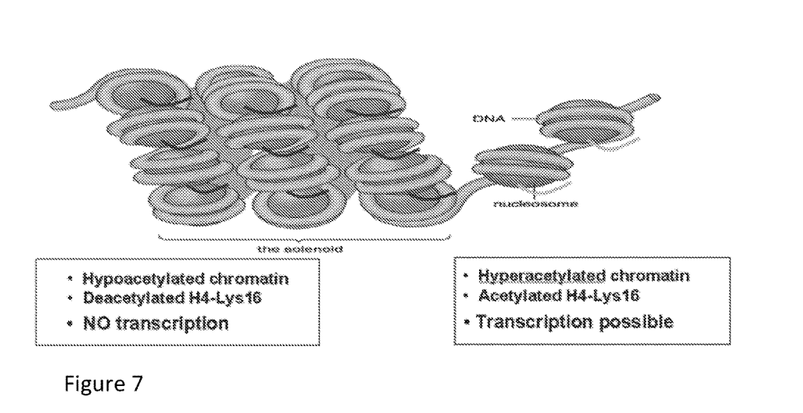
FIG. 7. Schematic showing how Lunasin upregulates gene expression by increasing H4-Lys16 acetylation.
Figure 8:
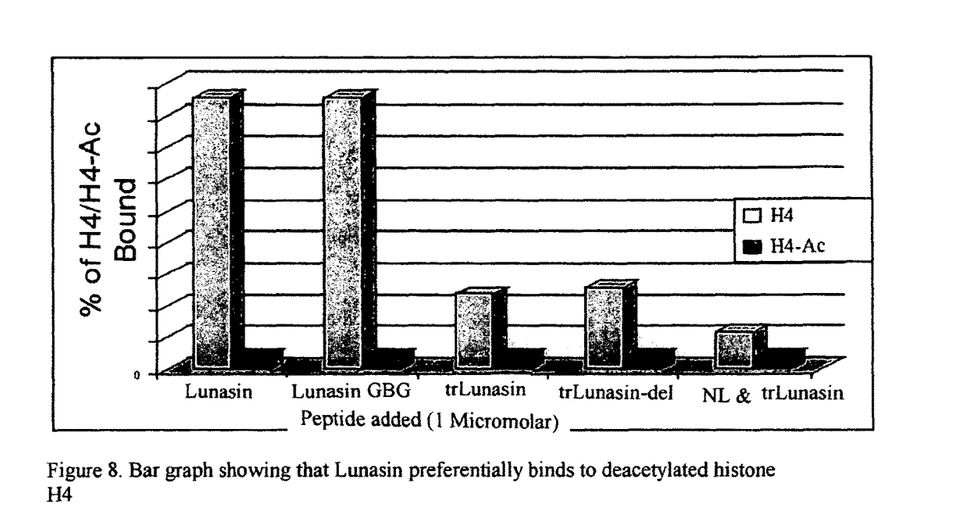
FIG. 8. Graph showing Lunasin preferentially binds to deacetylated histone H4.

See FIG. 5 that shows a Western blot of THBS and PCR of ChIP DNA isolated with anti-Ac-H4 Lys16. THBS protein levels were determined in RWPE-1 and -2 cell lines treated with or without lunasin. PCR was conducted on ChIP DNA isolated with acetylated H4-Lys16 antibody, using primers derived from the promoter and exon 11 of the THBS gene.

Example 3

A. In Vitro Histone Acetylation (HAT) Assay

Acid extracted histones from untreated Hela cells and purified recombinant histone H4 are used as templates in an in vitro histone acetylation (HAT) assay. Histone templates are pre-incubated in the presence or absence of 2 µM lunasin peptide for 30 min at RT before the addition of acetyl co-A, HAT reaction buffer and histone acetylase enzymes (p300, HAT1 and PCAF). HAT reaction mixture is incubated with shaking at 30° C. for 1 h before stopping the reaction by adding protein sample buffer and boiling for 5 min. Samples are run on 10-20% SDS-PAGE gels, blotted onto nitrocellulose membranes and immunostained with antibodies against histone H4 with specific N-terminal lysine acetylation sites at Lys 4, 8, 12 and 16. Densitometer readings are normalized using signals from untreated histone templates.

B. Cell Culture Experiments

HepG2 liver cells are grown in cell culture in the presence or absence of 10 uM lunasin peptide. After 24 h exposure, cells are harvested and total protein and RNA are harvested. Western blots are immunostained with UGT1A1 antibody and densitometer signals normalized using actin controls. RT-PCR using total RNA and primers specific to the 9 members of the UGT1A family of proteins are conducted to identify upregulated and activated gene products as modulated by lunasin treatment. Real-time quantitative RT-PCR will be conducted to measure differences in transcription levels.

C. Results and Discussion

Results of this experiment indicate that Lunasin can upregulate expression of genes by binding to deacetylated Lysine 8 (Lys 8) of the N-terminal tail of histone H4 and then changing the structural conformation of the H4 tail to allow increased acetylation of Lysine 16 (Lys16) by histone acetylase enzymes. Acetylation of Lys 16 in the H4 N-terminal tail has been shown in X-ray crystallography and mutation analyses to be involved in creating the "open" conformation of chromatin required for transcription activation of gene expression. Immunostaining studies done on HepG2 liver cells using UGT1A1 primary antibody, show that the addition of 10 µM of lunasin to the growth media can upregulate expression levels of UGT1A1. RT-PCR using primers specific to UGT1A family of genes revealed the significant upregulation of UGT1A1, UGT1A3, UGT1A6 and UGT1A10. The results suggest that upregulation of these UGT1A genes by lunasin through chromatin remodeling (increased H4-Lysine 16 acetylation) leads to the significant reduction of PhIP-induced prostate cancer formation in rats.

Example 4

A. Bisulfite Sequencing of THBS-1 Gene Promoter Region.

Figure 10:
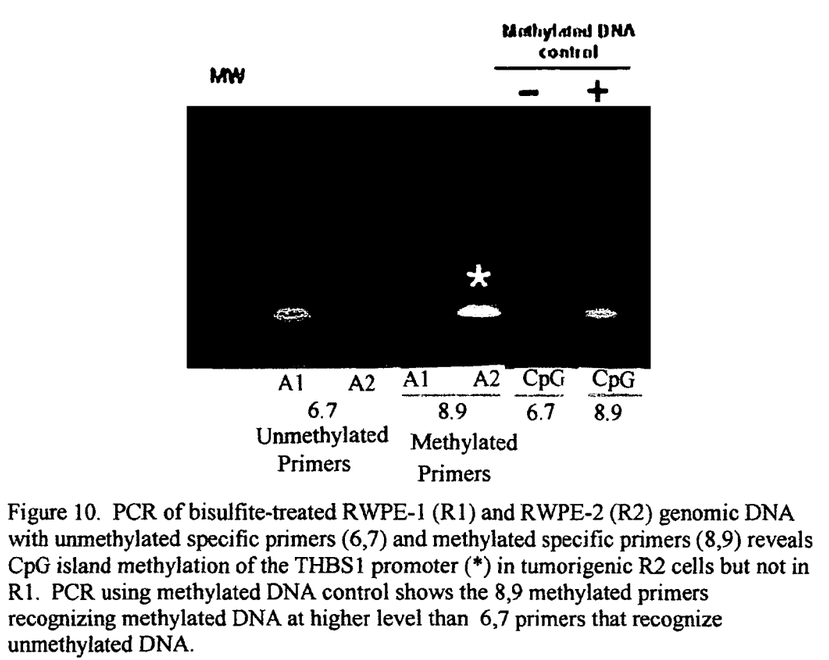
FIG. 10. PCR of bisulfite-treated RWPE-1 (R1) (SEQ ID No.1) and RWPE-2 (R2) (SEQ ID No.2) genomic DNA with unmethylated specific primers and methylated specific primers reveals CpG island methylation of the THBS1 promoter (*) in tumorigenic R2 cells but not in R1. PCR using methylated DNA control shows the 8,9 methylated primers recognizing methylated DNA at higher level than 6,7 primers that recognize unmethylated DNA.

Bioinformatic analysis of the 121 genes upregulated by lunasin in normal prostate cells shows that more than a third of the genes are located from 0 to 2000 bp (10 nucleosomes away) from a CpG island which is highly significant when compared with random distribution of genes in the genome. Increased cytosine methylation of the CpG island is a characteristic epigenetic marker associated with cancer formation. To determine if the chemopreventive genes upregulated by lunasin in non-tumorigenic prostate cells undergo CpG island methylation that leads to hypoacetylation and loss of H4-Lys 16 acetylation, we conducted bisulfite specific PCR (BSP) and bisulfite sequencing of the promoter and first exon of THBS1 which contains a known CpG island. See FIG. 9 showing that Approximately 30% of genes upregulated by lunasin have transcription start sites within proximity to CpG islands in the human genome. The set of 121 genes upregulated by lunasin has significantly more CpG island in proximity to the transcription start site (0-2000 bp) compared to 7 randomly selected set of 121 genes (rnd1-7)) from the same microarray. Chi-square P value <0.005. Genomic DNA was isolated from RWPE-1 and RWPE-2 cells, and 500 ng was subjected to bisulfite conversion (EZ DNA-Methylation-Direct, Zymo Research, Orange, Calif.). Bisulfite reagent converts unmethylated cytosines to thymines, while methylated cytosines that follows a guanine (CpG) remain intact and are compared to known sequence for methylation status. Bisulfite-converted genomic DNA was subjected to bisulfite specific PCR (BSP) using primer sets designed using Methyl-Primer Express v1.0 software. Bisulfite specific PCR primers (BSP) were designed to be between 18 and 27 bases in length, have Tm between 56 and 64° C., no more than 500 bases upstream of transcription start site, through first exon. Using unmethylated primers specific to the promoter of THBS-1 and bisulfite treated RWPE-1 and RWPE-2 genomic DNA, PCR amplification products were more predominant in RWPE-1, indicating that the CpG island in the THBS-1 transcription start site is not methylated. On the other hand, the use of methylation specific primers within the same region of the THBS-1 promoter in PCR of bisulfite-treated genomic DNA, showed significantly more amplification products in RWPE-2, indicating that the CpG island in the THBS-1 promoter of the tumorigenic cell line RWPE-2 is highly methylated. The use of methylated genomic DNA as control, confirmed the efficacy of the methylation specific primers in detecting CpG island methylation in the THBS-1 promoter of RWPE-2. See FIG. 10. PCR of bisulfite-treated RWPE-1 (R1) and RWPE-2 (R2) genomic DNA with unmethylated specific primers (6,7) and methylated specific primers (8,9) reveals CpG island methylation of the THBS1 promoter (*) in tumorigenic R2 cells but not in R1. PCR using methylated DNA control shows the 8,9 methylated primers recognizing methylated DNA at higher level than 6,7 primers that recognize unmethylated DNA.

PCR, Cloning and Sequencing of Bisulfite Treated Genomic DNA

Bisulfite-converted genomic DNA from RWPE-1 and RWPE-2 was subjected to bisulfite specific PCR (BSP) using primer sets specific for the CpG island found in the promoter and first exon of THBS1. PCR was carried out in 25 μl reactions using hot-start methods (Taq PCR Kit, New England Biolabs, Ipswich, Mass.). Reverse primers were added just prior to PCR initiation to reduce primer dimer incidence. Reactions were run on 1.5-2% ethidium bromide-stained agarose gels and run at 100V for 45-60 minutes. PCR fragments were purified (Gel Extraction Kit, Qiagen Corp, Valencia, Calif.), ligated to pCR4-TOPO vector (TOPO-TA Cloning, Invitrogen Corp.) transformed into DH5α *E. coli* (Zymo Research) cells for cloning and incubated overnight on ampicillin+ LB-agar plates. Transformed colonies were grown overnight in ampicillin+ LB medium, and subsequently purified (Plasmid Mini-prep, Qiagen Corp). 2 μl purified plasmid was subjected to PCR and 1 μl plasmid subjected to EcoRI (New England Biolabs) restriction digest to screen for insert. Insert-containing plasmids were sent to Davis Sequencing (Davis, Calif.) for sequencing analysis using M13F primer set. Sequences were compared with known sequence data from the UCSC Genome Browser. Resultant THBS-1 promoter sequence of bisulfite treated RWPE-1 genomic DNA showed no CpG methylation. In the RWPE-2 cells, resultant sequence of the whole CpG island found within the promoter and first exon of THBS-1 showed varying degrees of methylation throughout this region of the THBS-1 gene. Most of the potential methylation sites were in the CpG islands, with few exceptions. These exceptions may be due to actual methylation or errors brought about by incomplete bisulfite conversion. It should be noted though that there were some methylation site overlap between cloned DNAs in RWPE-2, and not all of these methylation sites showed up when different primers and RWPE-2 genomic DNAs were used, indicating that RWPE-2 cells have varying methylation levels. The CpG methylation map in RWPE-2 shows the location of most CpGs that were found methylated in the different bisulfite treated genomic DNAs extracted from RWPE-2.

Figure 11:
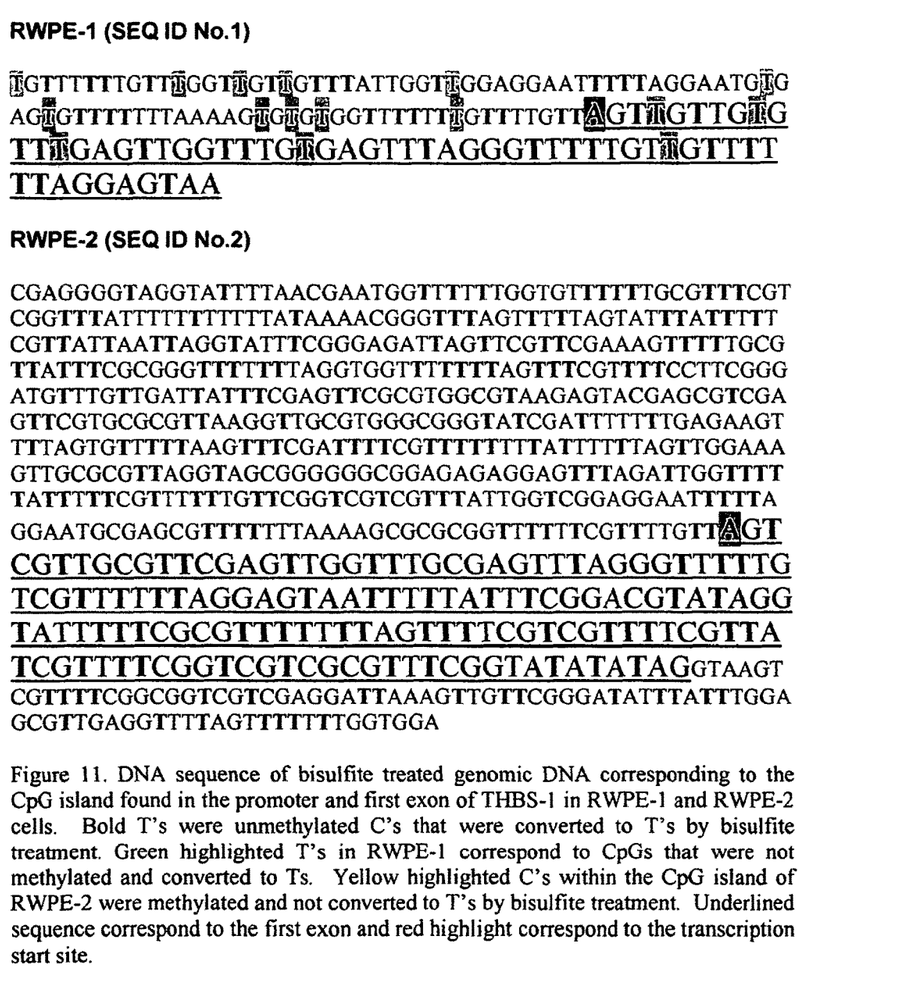
FIG. 11. DNA sequence of bisulfite treated genomic DNA corresponding to the CpG island found in the promoter and first exon of THBS-1 in RWPE-1 (SEQ ID No.1) and RWPE-2 (SEQ ID No.2) cells. Bold T's were unmethylated C's that were converted to T's by bisulfite treatment. Green highlighted T's in RWPE-1 correspond to CpGs that were not methylated and converted to Ts. Yellow highlighted C's within the CpG island of RWPE-2 were methylated and not converted to T's by bisulfite treatment. Underlined sequence correspond to the first exon and red highlight correspond to the transcription start site.

See FIG. 11 that shows DNA sequence of bisulfite treated genomic DNA corresponding to the CpG island found in the promoter and first exon of THBS-1 in RWPE-1 and RWPE-2 cells. Bold T's were unmethylated C's that were converted to T's by bisulfite treatment. Green highlighted T's in RWPE-1 correspond to CpGs that were not methylated and converted to Ts. Yellow highlighted C's within the CpG island of RWPE-2 were methylated and not converted to T's by bisulfite treatment. Underlined sequence correspond to the first exon and red highlight correspond to the transcription start site.

Various Embodiments of the Invention

The present invention encompasses various embodiments including gene expression profiles produced in response to lunasin exposure. Such gene expression profiles correlate with anti-neoplastic activity at a cellular level and can be used in methods for screening potential anti-neoplastic agents. Additionally, these gene expression profiles can be used in methods for treatment (both prophylactic and active) and in monitoring of a subject having a neoplastic disease or having a risk factor for a neoplastic disease. Additionally, the invention includes microarrays used to measure the expression of particular sets of genes.

The present invention encompasses methods for identification of diet-influenced epigenetic modifications of the human genome and provides a new mechanism to elucidate: 1) the effects of low potency food bioactives on regulatory genetic networks and physiological pathways and, 2) how they can have profound effects over time by 'reprogramming' the epigenome to promote health and prevent disease.

The present disclosure describes how transfection of lunasin gene in mammalian cells causes anti-mitosis and apoptosis; how lunasin peptide inhibits oncogene and carcinogen-induced tumor formation; and how Lunasin acts as a chemopreventative agent.

The invention encompasses a method for screening a test compound for anti-neoplastic activity, the method comprising: providing a cell, measuring expression by the cell of a plurality of genes, exposing the cell to the test compound, and re-measuring the expression by the cell of the plurality of genes, wherein the degree of increase in expression of the plurality of genes corresponds to the degree of anti-neoplastic activity of the test compound. In certain embodiments, the degree of increase of gene expression of the plurality of genes is measured using a weighted average. This method commonly employs an array (or microarray) comprising a substrate and a plurality of polynucleotide probes affixed to the substrate. The array generally comprises a plurality of polynucleotide probes that are specifically complementary to a plurality of genes as shown in Table 1.

The invention also encompasses a method for treatment and monitoring of a subject having a neoplastic disease. The method comprises administering lunasin (or related or derived compounds) to the subject, and monitoring the change in expression levels of at least one gene selected from a set of genes known to be up-regulated by lunasin.

The invention further encompasses a method for prophylactically treating and monitoring a subject having one of more cancer risk factors. The method comprises administering lunasin (or related or derived compounds) and monitoring expression levels of at least one gene selected from a set of genes known to be up-regulated by lunasin.

The invention further encompasses a method for monitoring anti-neoplastic activity in cell culture or in a subject during treatment (reactive or prophylactic). The method comprises taking a baseline reading of gene expression for at least one gene selected from a set of genes known to be up-regulated by lunasin; administering lunasin (or a derived or related compound, or providing some other treatment to the subject or cell culture); and then re-measuring the expression of at least one of the genes being monitored. Such a method may be useful for research to determine the efficacy of various drugs.

The invention also includes microarrays comprising a set of genes selected from the 123 genes shown in this disclosure to be up-regulated by lunasin by at least two-fold.

The invention also includes methods for preventing neoplastic growth in an organism comprising administering an agent, wherein the agent up-regulates the activity or expression of at least one, two, three, four, five, six or more genes selected from the 123 genes shown in this disclosure to be up-regulated by lunasin by at least two-fold. The agent is generally lunasin or a related or derived compound.

TABLE 1

Complete list of genes up-regulated in normal RWPE-1 epithelial cells (Section A) and in Tumorigenic prostate RWPE-2 epithelial cells (Section A), after 24 hour exposure to lunasin.

| | Affymetrix probe sets | Gene identifiers | Gene Name (Note: EASE version 2.0 was used for annotation) | Official Gene Symbol |
|---|---|---|---|---|
| | | | A. Genes up-regulated in non-tumorigenic prostate epithelial cell line (RWPE-1) | |
| 1 | 200914_x_at | 3895 | kinectin 1 (kinesin receptor) | KTN1 |
| 2 | 201730_s_at | 7175 | translocated promoter region (to activated MET oncogene) | TPR |
| 3 | 200915_x_at | 3895 | kinectin 1 (kinesin receptor) | KTN1 |
| 4 | 213229_at | 23405 | Dicer1, Dcr-1 homolog (*Drosophila*) | DICER1 |
| 5 | 200050_at | 7705 | zinc finger protein 146 | ZNF146 |
| 6 | 201667_at | 2697 | gap junction protein, alpha 1, 43 kDa (connexin 43) | GJA1 |
| 7 | 201699_at | 5706 | proteasome (prosome, macropain) 26S subunit, ATPase, 6 | PSMC6 |
| 8 | 204455_at | 667 | bullous pemphigoid antigen 1, 230/240 kDa | BPAG1 |
| 9 | 208896_at | 8886 | DEAD (Asp-Glu-Ala-Asp) box polypeptide 18 | DDX18 |
| 10 | 200603_at | 5573 | protein kinase, cAMP-dependent, regulatory, type I, alpha (tissue specific extinguisher 1) | PRKAR1A |
| 11 | 212648_at | 54505 | DEAH (Asp-Glu-Ala-His) box polypeptide 29 | DHX29 |
| 12 | 216268_s_at | 182 | jagged 1 (Alagille syndrome) | JAG1 |
| 13 | 218181_s_at | 54912 | hypothetical protein FLJ20373 | |
| 14 | 219918_s_at | 259266 | asp (abnormal spindle)-like, microcephaly associated (*Drosophila*) | ASPM |
| 15 | 203789_s_at | 10512 | sema domain, immunoglobulin domain (Ig), short basic domain, secreted, (semaphorin) 3C | SEMA3C |
| 16 | 217975_at | 51186 | pp21 homolog | |
| 17 | 204240_s_at | 10592 | SMC2 structural maintenance of chromosomes 2-like 1 (yeast) | SMC2L1 |
| 18 | 202169_s_at | 60496 | aminoadipate-semialdehyde dehydrogenase-phosphopantetheinyl transferase | AASDHPPT |
| 19 | 214709_s_at | 3895 | kinectin 1 (kinesin receptor) | KTN1 |
| 20 | 221802_s_at | 57698 | KIAA1598 protein | |
| 21 | 201713_s_at | 5903 | RAN binding protein 2 | RANBP2 |
| 22 | 212629_s_at | 5586 | protein kinase C-like 2 | PRKCL2 |
| 23 | 220085_at | 3070 | helicase, lymphoid-specific | HELLS |
| 24 | 213168_at | 6670 | Sp3 transcription factor | SP3 |
| 25 | 212888_at | 23405 | Dicer1, Dcr-1 homolog (*Drosophila*) | DICER1 |
| 26 | 212245_at | 90411 | multiple coagulation factor deficiency 2 | MCFD2 |
| 27 | 213294_at | | hypothetical protein FLJ38348 | |
| 28 | 208808_s_at | 3148 | high-mobility group box 2 | HMGB2 |
| 29 | 202704_at | 10140 | transducer of ERBB2, 1 | TOB1 |
| 30 | 212582_at | 114882 | oxysterol binding protein-like 8 | OSBPL8 |
| 31 | 202381_at | 8754 | a disintegrin and metalloproteinase domain 9 (meltrin gamma) | ADAM9 |
| 32 | 212640_at | | hypothetical protein LOC201562 | |
| 33 | 211953_s_at | 3843 | karyopherin (importin) beta 3 | KPNB3 |
| 34 | 205596_s_at | 64750 | E3 ubiquitin ligase SMURF2 | SMURF2 |
| 35 | 211929_at | 10151 | heterogeneous nuclear ribonucleoprotein A3 | HNRPA3 |
| 36 | 201889_at | 10447 | family with sequence similarity 3, member C | FAM3C |
| 37 | 203820_s_at | 10643 | IGF-II mRNA-binding protein 3 | |
| 38 | 208731_at | 5862 | RAB2, member RAS oncogene family | RAB2 |
| 39 | 211967_at | 114908 | pro-oncosis receptor inducing membrane injury gene | PORIMIN |
| 40 | 217945_at | 53339 | BTB (POZ) domain containing 1 | BTBD1 |
| 41 | 211257_x_at | 27332 | NP220 nuclear protein | |

TABLE 1-continued

Complete list of genes up-regulated in normal RWPE-1 epithelial cells (Section A) and in Tumorigenic prostate RWPE-2 epithelial cells (Section A), after 24 hour exposure to lunasin.

| | Affymetrix probe sets | Gene identifiers | Gene Name (Note: EASE version 2.0 was used for annotation) | Official Gene Symbol |
|---|---|---|---|---|
| 42 | 212250_at | | LYRIC/3D3 | |
| 43 | 207941_s_at | 9584 | RNA-binding region (RNP1, RRM) containing 2 | RNPC2 |
| 44 | 200605_s_at | 5573 | protein kinase, cAMP-dependent, regulatory, type I, alpha (tissue specific extinguisher 1) | PRKAR1A |
| 45 | 201486_at | 5955 | reticulocalbin 2, EF-hand calcium binding domain | RCN2 |
| 46 | 217941_s_at | 55914 | erbb2 interacting protein | ERBB2IP |
| 47 | 203755_at | 701 | BUB1 budding uninhibited by benzimidazoles 1 homolog beta (yeast) | BUB1B |
| 48 | 201242_s_at | 481 | ATPase, Na+/K+ transporting, beta 1 polypeptide | ATP1B1 |
| 49 | 201737_s_at | 10299 | similar to S. cerevisiae SSM4 | |
| 50 | 221773_at | 2004 | ELK3, ETS-domain protein (SRF accessory protein 2) | ELK3 |
| 51 | 217816_s_at | 57092 | PEST-containing nuclear protein | |
| 52 | 209187_at | 1810 | down-regulator of transcription 1, TBP-binding (negative cofactor 2) | DR1 |
| 53 | 202760_s_at | 11217 | A kinase (PRKA) anchor protein 2 | AKAP2 |
| 54 | 212352_s_at | 10972 | transmembrane trafficking protein | |
| 55 | 213285_at | NA | hypothetical protein LOC161291 | |
| 56 | 212692_s_at | 987 | LPS-responsive vesicle trafficking, beach and anchor containing | LRBA |
| 57 | 212718_at | 27249 | hypothetical protein CL25022 | |
| 58 | 209259_s_at | 9126 | chondroitin sulfate proteoglycan 6 (bamacan) | CSPG6 |
| 59 | 201595_s_at | 55854 | likely ortholog of mouse immediate early response, erythropoietin 4 | |
| 60 | 202551_s_at | 51232 | cysteine-rich motor neuron 1 | CRIM1 |
| 61 | 218067_s_at | 55082 | hypothetical protein FLJ10154 | |
| 62 | 211945_s_at | 3688 | integrin, beta 1 (fibronectin receptor, beta polypeptide, antigen CD29 includes MDF2, MSK12) | ITGB1 |
| 63 | 209025_s_at | 10492 | synaptotagmin binding, cytoplasmic RNA interacting protein | SYNCRIP |
| 64 | 202599_s_at | 8204 | nuclear receptor interacting protein 1 | NRIP1 |
| 65 | 201991_s_at | 3799 | kinesin family member 5B | KIF5B |
| 66 | 202413_s_at | 7398 | ubiquitin specific protease 1 | USP1 |
| 67 | 209422_at | 51230 | chromosome 20 open reading frame 104 | C20orf104 |
| 68 | 201132_at | 3188 | heterogeneous nuclear ribonucleoprotein H2 (H') | HNRPH2 |
| 69 | 214055_x_at | 23215 | HBxAg transactivated protein 2 | |
| 70 | 203743_s_at | 6996 | thymine-DNA glycosylase | TDG |
| 71 | 211969_at | 3320 | heat shock 90 kDa protein 1, alpha | HSPCA |
| 72 | 204059_s_at | 4199 | malic enzyme 1, NADP(+)-dependent, cytosolic | ME1 |
| 73 | 221505_at | 81611 | acidic (leucine-rich) nuclear phosphoprotein 32 family, member E | ANP32E |
| 74 | 212408_at | 26092 | lamina-associated polypeptide 1B | |
| 75 | 212615_at | 80205 | hypothetical protein FLJ12178 | |
| 76 | 218577_at | 55631 | hypothetical protein FLJ20331 | |
| 77 | 201735_s_at | 1182 | chloride channel 3 | CLCN3 |
| 78 | 200995_at | 10527 | importin 7 | IPO7 |
| 79 | 217758_s_at | 56889 | SM-11044 binding protein | |
| 80 | 201505_at | 3912 | laminin, beta 1 | LAMB1 |
| 81 | 201690_s_at | 7163 | tumor protein D52 | TPD52 |
| 82 | 203362_s_at | 4085 | MAD2 mitotic arrest deficient-like 1 (yeast) | MAD2L1 |
| 83 | 202277_at | 10558 | serine palmitoyltransferase, long chain base subunit 1 | SPTLC1 |
| 84 | 208783_s_at | 4179 | membrane cofactor protein (CD46, trophoblast-lymphocyte cross-reactive antigen) | MCP |
| 85 | 217523_at | | Data not available | |
| 86 | 204822_at | 7272 | TTK protein kinase | TTK |
| 87 | 218542_at | 55165 | chromosome 10 open reading frame 3 | C10orf3 |
| 88 | 201939_at | 10769 | serum-inducible kinase | |
| 89 | 204976_s_at | 9949 | Alport syndrome, mental retardation, midface hypoplasia and elliptocytosis chromosomal region, gene 1 | AMMECR1 |
| 90 | 202234_s_at | 6566 | solute carrier family 16 (monocarboxylic acid transporters), member 1 | SLC16A1 |
| 91 | 204258_at | 1105 | chromodomain helicase DNA binding protein 1 | CHD1 |
| 92 | 201862_s_at | 9208 | leucine rich repeat (in FLII) interacting protein 1 | LRRFIP1 |
| 93 | 213070_at | 6165 | ribosomal protein L35a | RPL35A |
| 94 | 204058_at | 4199 | malic enzyme 1, NADP(+)-dependent, cytosolic | ME1 |
| 95 | 201734_at | | chloride channel 3 | CLCN3 |
| 96 | 209272_at | 4664 | NGFI-A binding protein 1 (EGR1 binding protein 1) | NAB1 |
| 97 | 201745_at | 5756 | PTK9 protein tyrosine kinase 9 | PTK9 |
| 98 | 213729_at | 55660 | formin binding protein 3 | FNBP3 |
| 99 | 209115_at | 9039 | ubiquitin-activating enzyme E1C (UBA3 homolog, yeast) | UBE1C |
| 100 | 201849_at | 664 | BCL2/adenovirus E1B 19 kDa interacting protein 3 | BNIP3 |
| 101 | 212455_at | 91746 | splicing factor YT521-B | |
| 102 | 201689_s_at | 7163 | tumor protein D52 | TPD52 |
| 103 | 201110_s_at | 7057 | thrombospondin 1 | THBS1 |
| 104 | 212149_at | 23167 | KIAA0143 protein | |

TABLE 1-continued

Complete list of genes up-regulated in normal RWPE-1 epithelial cells (Section A) and in Tumorigenic prostate RWPE-2 epithelial cells (Section A), after 24 hour exposure to lunasin.

| | Affymetrix probe sets | Gene identifiers | Gene Name (Note: EASE version 2.0 was used for annotation) | Official Gene Symbol |
|---|---|---|---|---|
| 105 | 212192_at | 115207 | potassium channel tetramerisation domain containing 12 | KCTD12 |
| 106 | 209476_at | 81542 | thioredoxin domain containing | TXNDC |
| 107 | 214363_s_at | 9782 | matrin 3 | MATR3 |
| 108 | 201567_s_at | 2803 | golgi autoantigen, golgin subfamily a, 4 | GOLGA4 |
| 109 | 200626_s_at | 9782 | matrin 3 | MATR3 |
| 110 | 203804_s_at | 10414 | acid-inducible phosphoprotein | |
| 111 | 200977_s_at | 8887 | Tax1 (human T-cell leukemia virus type I) binding protein 1 | TAX1BP1 |
| 112 | 212893_at | 26009 | zinc finger, ZZ domain containing 3 | ZZZ3 |
| 113 | 201435_s_at | 1977 | eukaryotic translation initiation factor 4E | EIF4E |
| 114 | 215548_s_at | 23256 | sec1 family domain containing 1 | SCFD1 |
| 115 | 212248_at | | LYRIC/3D3 | |
| 116 | 201398_s_at | 23471 | translocation associated membrane protein 1 | TRAM1 |
| 117 | 201304_at | 4698 | NADH dehydrogenase (ubiquinone) 1 alpha subcomplex, 5, 13 kDa | NDUFA5 |
| 118 | 203987_at | 8323 | frizzled homolog 6 (Drosophila) | FZD6 |
| 119 | 208925_at | 56650 | chromosome 3 open reading frame 4 | C3orf4 |
| 120 | 204094_s_at | 9819 | KIAA0669 gene product | |
| 121 | 200989_at | 3091 | hypoxia-inducible factor 1, alpha subunit (basic helix-loop-helix transcription factor) | HIF1A |

B. Genes up-regulated in tumorigenic prostate epithelial cell line (RWPE-2)

| 1 | 203325_s_at | 1289 | collagen, type V, alpha 1 | COL5A1 |
| 2 | 201551_s_at | 3916 | lysosomal-associated membrane protein 1 | LAMP1 |

TABLE 2

Partial list of genes up-regulated in normal epithelial cells (RWPE-1) after 24 hour exposure to 2 micromolar lunasin, organized by gene function.

| | Unigene cluster | Gene ID | Symbol | Fold-change |
|---|---|---|---|---|
| a) Tumor suppressive (anti-proliferative) genes | | | | |
| protein kinase, cAMP-dependent, regulatory, type I, alpha | Hs.280342 | 5573 | PRKAR1A, PKA | 2.45 |
| transducer of ERBB2, 1 | Hs.178137 | 10140 | TOB1 | 2.32 |
| erbb2 interacting protein | Hs.8117 | 55914 | ERBB2IP, ERBIN | 2.23 |
| b) Genes involved in apoptosis | | | | |
| Protein kinase C-like 2 | Hs.69171 | 5586 | PRKCL2, PRK2 | 2.33 |
| BCL2/adenovirus E1B 19 kDa interacting prot. 3 | Hs.79428 | 664 | BNIP3, NIP3 | 2.05 |
| thrombospondin 1 | Hs.164226 | 7057 | THBS1, TSP1 | 2.05 |
| pro-oncosis receptor inducing membrane injury gene | Hs.172089 | 114908 | PORIMIN | 2.26 |
| serine palmitoyltransferase, long chain base subunit 1 | Hs.90458 | 10558 | SPTLC1 | 2.12 |
| c) Mitotic checkpoint control genes | | | | |
| BUB1 budding uninhibited by benzimidazoles 1 homolog beta (yeast) | Hs.36708 | 701 | BUB1B, BUBR1 | 2.23 |
| TTK protein kinase | Hs.169840 | 7272 | TTK | 2.08 |
| MAD2 mitotic arrest deficient-like 1 (yeast) | Hs.79078 | 4085 | MAD2L1 | 2.12 |
| d) Protein degradation genes | | | | |
| Proteasome (prosome, macropain) 26S subunit, ATPase, 6 | Hs.156171 | 5706 | PSMC6 | 2.58 |
| RAN binding protein 2 | Hs.199179 | 5903 | RANBP2 | 2.36 |
| E3 ubiquitin ligase SMURF2 | Hs.438968 | 64750 | SMURF2 | 2.29 |
| Ubiquitin specific protease 1 | Hs.35086 | 7398 | USP1 | 2.23 |
| Ubiquitin-activating enzyme E1C (UBA3 homolog, yeast) | Hs.154320 | 9039 | UBE1C | 2.15 |

The invention claimed is:

1. A method for screening a test compound for anti-neoplastic activity, the method comprising: providing a test compound, providing a cell, measuring and quantifying the degree of increase in the acetylation of Lysine 16 of the N-terminal tail of histone H4, exposing the cell to the test compound, and re-measuring the acetylation of Lysine 16 of the N-terminal tail of histone H4 in the cell, wherein the method further comprises measuring the expression of UGT1A and THBS, both before and after exposure to the test compound, wherein a two-fold increase in acetylation of Lysine 16 of the N-terminal tail of histone H4, together with an increased level of expression of UGT1A and THBS corresponds to the classification of the test compound as putatively having anti-neoplastic activity.

2. The method of claim 1 wherein the test compound is a variant or derivative of lunasin.

3. The method of claim 1 wherein the cell is an RWPE cell.

4. The method of claim 1 further comprising measuring the degree of methylation of nucleotides within the CpG island in the promoter region of the thrombospondin gene before and after exposure of the cell to the test compound, wherein a decrease in methylation corresponds to the classification of the test compound as putatively having anti-neoplastic activity.

5. The method of claim 1 wherein the test compound is a soybean protein.

6. The method of claim 1 further comprising measuring the expression of the chemopreventative gene UGT1A, before and after exposure to the test compound, wherein increased expression corresponds to the classification of the test compound as putatively having anti-neoplastic activity.

7. The method of claim 1 further comprising measuring the expression of the chemopreventative thrombospondin gene (THBS), before and after exposure to the test compound, wherein increased expression corresponds to the classification of the test compound as putatively having anti-neoplastic activity.

8. The method of claim 1 wherein the cell is derived from prostate tissue.

* * * * *

UNITED STATES PATENT AND TRADEMARK OFFICE
CERTIFICATE OF CORRECTION

| | | |
|---|---|---|
| PATENT NO. | : 9,678,060 B2 | Page 1 of 1 |
| APPLICATION NO. | : 12/682892 | |
| DATED | : June 13, 2017 | |
| INVENTOR(S) | : Raymond Rodriguez and Alfredo F. Galvez | |

It is certified that error appears in the above-identified patent and that said Letters Patent is hereby corrected as shown below:

In the Specification

In Column 1, Line 23, cancel the text beginning with "under one or more grants" and ending with "the National Institutes of Health (NIH)." in Line 26 and insert the following:

--by the National Institutes of Health (NIH) Award No. P60MD0022 and the U.S. Army Medical Research and Materiel Command (MRCR) Award No. W81XWH-07-1-0433.--

Signed and Sealed this
Twenty-first Day of November, 2017

Joseph Matal
*Performing the Functions and Duties of the
Under Secretary of Commerce for Intellectual Property and
Director of the United States Patent and Trademark Office*